(12) United States Patent
Lai et al.

(10) Patent No.: US 10,563,185 B1
(45) Date of Patent: Feb. 18, 2020

(54) BETA-GLUCOSIDASE HAVING IMPROVED ENZYMATIC ACTIVITY

(71) Applicant: Dongguan APAC Biotechnology CO., Ltd., DongGuan, Guandong (CN)

(72) Inventors: Hui-Lin Lai, New Taipei (TW);
Ya-Shan Cheng, New Taipei (TW);
Tzu-Hui Wu, New Taipei (TW);
Cheng-Yen Lin, New Taipei (TW);
Ting-Yung Huang, New Taipei (TW);
I-Hsuan Lin, New Taipei (TW);
Cheng-Bin Zheng, New Taipei (TW)

(73) Assignee: DONGGUAN APAC BIOTECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 16/363,863

(22) Filed: Mar. 25, 2019

(51) Int. Cl.
*C12N 9/24* (2006.01)

(52) U.S. Cl.
CPC .... *C12N 9/2402* (2013.01); *C12Y 302/01021* (2013.01)

(58) Field of Classification Search
None
See application file for complete search history.

(56) References Cited

FOREIGN PATENT DOCUMENTS

WO    WO-2009108941 A2 *  9/2009    ......... C12N 15/8214

* cited by examiner

*Primary Examiner* — Paul J Holland
(74) *Attorney, Agent, or Firm* — Kirton McConkie; Evan R. Witt

(57) ABSTRACT

A beta-glucosidase having improved enzymatic activity is disclosed. The amino acid sequence of the beta-glucosidase is a modified amino acid sequence of SEQ ID NO: 2, wherein the modification is a substitution of tyrosine at position 286 with phenylalanine, or a substitution of asparagine at position 639 with glutamate.

6 Claims, 7 Drawing Sheets

Specification includes a Sequence Listing.

FIG. 1

| Mutant | Mutagenic Primer Sequence |
|--------|---------------------------|
| Y286F | 5'-TATGCCGGGAGACGTCGATTTCGACAGTGGCA-3'<br>(SEQ ID NO: 3) |
| N639E | 5'-TATGGTCTGAGCTACACCACCTTTGAATACTCGAACCTT-3'<br>(SEQ ID NO: 4) |

SEQUENCE LISTING

<160> NUMBER OF SEQ ID NOS: 8

<210> SEQ ID NO 1
<211> LENGTH: 2526
<212> TYPE: DNA
<213> ORGANISM: Aspergillus niger SH2

<400> SEQUENCE: 1

| | |
|---|---|
| gatgaattgg cctactcccc tccatactac ccatctccat gggctaacgg tcaaggtgat | 60 |
| tgggctgaag cttaccaaag agctgttgat attgtttctc aaatgacttt ggctgaaaag | 120 |
| gttaacttga ctactggtac tggttgggaa ttggaattgt gtgttggtca aactggtggt | 180 |
| gttccaagat tgggtattcc aggtatgtgt gctcaagatt ctccattggg tgttagagat | 240 |
| tctgactaca actctgcgtt ccctgccggt gtcaacgtgg ccgcaacctg ggacaagaat | 300 |
| ctggcttacc ttcgtggcca ggctatgggt caggagttta gtgacaaggg tgctgatatc | 360 |
| caattgggtc cagctgccgg ccctctcggt agaagtcccg acggcggtcg taactgggag | 420 |
| ggcttctccc ccgacccggc cctcagtggt gtgctctttg cagagacaat caagggtatt | 480 |
| caggatgctg gtgtggttgc aacgctaag cactacatcg cctacgagca ggagcatttc | 540 |
| cgtcaggcgc ctgaagctca aggctacgga ttcaatatta ccgagagtgg aagcgcgaac | 600 |
| ctcgacgata agactatgca tgagctgtac ctctggccct cgcggatgc catccgtgca | 660 |
| ggtgccggtg ctgtgatgtg ctcgtacaac cagatcaaca acagctatgg ctgccaaaac | 720 |
| agctacactc tgaacaagct gctcaaggct gagctgggtt ccagggctt tgtcatgagt | 780 |
| gattgggcgg ctcaccatgc cggtgtgagt ggtgctttgg cgggattgga catgtctatg | 840 |
| ccgggagacg tcgattacga cagtggcacg tcttactggg gtaccaactt gaccatcagt | 900 |
| gtgctcaacg ggacggtgcc ccaatggcgt gttgatgaca tggctgtccg catcatggcc | 960 |
| gcctactaca aggtcggccg tgaccgtctg tggactcctc ccaacttcag ctcatggacc | 1020 |
| agagatgaat acggcttcaa gtactactat gtctcggagg gaccgtatga aaggtcaac | 1080 |
| cagttcgtga acgtgcaacg caaccatagc gagttgatcc gccgtattgg agcagacagc | 1140 |
| acggtgctcc tcaagaacga tggcgctctt cccttgactg gaaaggagcg cttggtcgcc | 1200 |
| cttatcggag aagatgcggg ttccaatcct tatggtgcca acggctgcag tgaccgtggg | 1260 |
| tgcgacaatg gaacattggc gatgggctgg ggaagtggca ctgccaactt tccctacttg | 1320 |
| gtgaccccg agcaggccat ctcgaacgag gtgctcaaga acaagaatgg cgtattcact | 1380 |
| gcgaccgata actgggctat tgatcagatt gaggcgcttg ctaagaccgc cagtgtctct | 1440 |
| cttgtctttg tcaacgccga ctctggtgag ggttatatca atgtcgacgg aaacctgggt | 1500 |
| gaccgcagga acctgaccct gtggaggaac ggcgacaatg tgatcaaggc tgctgctagc | 1560 |
| aactgcaaca cacgatcgt tattattcac tctgtcggcc cagtcttggt taacgagtgg | 1620 |
| tacgacaacc ccaatgttac cgctattctc tggggtggtc ttcccggtca ggagtctggc | 1680 |
| aactccctcg ccgacgtgct ctacggccgt gtcaaccccg tgccaagtc gcccttcacc | 1740 |
| tggggcaaga ctcgtgaggc ctaccaagat tacttgtaca ccgagcccaa caacggcaac | 1800 |
| ggagcgcccc aggaagactt cgtcgagggc gtcttcattg actaccgcgg atttgacaag | 1860 |
| cgcaacgaga ctcctatcta tgagttcggc tatggtctga gctacaccac cttcaactac | 1920 |
| tcgaaccttc aggtggaggt tctgagcgcc cctgcgtacg agcctgcttc gggcgagact | 1980 |
| gaggcagcgc cgactttcgg agaggtcgga aatgcgtcgg attacctcta ccccgatgga | 2040 |
| ctgcagagaa tcaccaagtt catctacccc tggctcaaca gtaccgatct tgaggcgtct | 2100 |

```
tctggggatg ctagctatgg gcaggatgcc tcagactatc ttcccgaggg agccaccgat   2160
ggctctgcgc aaccgatcct gcctgccggt ggtggtgctg gcggcaaccc tcgcctgtac   2220
gacgagctca tccgcgtgtc ggtgactatc aagaacaccg gcaaggttgc gggtgatgaa   2280
gttcctcaac tgtatgtttc tcttggcggc cctaacgaac ccaagatcgt gctgcgtcaa   2340
ttcgagcgta tcacgctgca gccgtcgaaa gagacgcagt ggagcacaac tctgacgcgc   2400
cgtgaccttg cgaactggaa tgttgagacg caggactggg agattacgtc gtatcccaag   2460
atggtgtttg ccggaagctc ctcgcggaag ctgccgctcc gggcgtctct gcctactgtt   2520
cactaa                                                             2526

<210> SEQ ID NO 2
<211> LENGTH: 841
<212> TYPE: PRT
<213> ORGANISM: Aspergillus niger SH2

<400> SEQUENCE: 2
```

Asp Glu Leu Ala Tyr Ser Pro Pro Tyr Tyr Pro Ser Pro Trp Ala Asn
1               5                   10                  15

Gly Gln Gly Asp Trp Ala Glu Ala Tyr Gln Arg Ala Val Asp Ile Val
            20                  25                  30

Ser Gln Met Thr Leu Ala Glu Lys Val Asn Leu Thr Thr Gly Thr Gly
        35                  40                  45

Trp Glu Leu Glu Leu Cys Val Gly Gln Thr Gly Gly Val Pro Arg Leu
    50                  55                  60

Gly Ile Pro Gly Met Cys Ala Gln Asp Ser Pro Leu Gly Val Arg Asp
65                  70                  75                  80

Ser Asp Tyr Asn Ser Ala Phe Pro Ala Gly Val Asn Val Ala Ala Thr
                85                  90                  95

Trp Asp Lys Asn Leu Ala Tyr Leu Arg Gly Gln Ala Met Gly Gln Glu
            100                 105                 110

Phe Ser Asp Lys Gly Ala Asp Ile Gln Leu Gly Pro Ala Ala Gly Pro
        115                 120                 125

Leu Gly Arg Ser Pro Asp Gly Gly Arg Asn Trp Glu Gly Phe Ser Pro
    130                 135                 140

Asp Pro Ala Leu Ser Gly Val Leu Phe Ala Glu Thr Ile Lys Gly Ile
145                 150                 155                 160

Gln Asp Ala Gly Val Val Ala Thr Ala Lys His Tyr Ile Ala Tyr Glu
                165                 170                 175

Gln Glu His Phe Arg Gln Ala Pro Glu Ala Gln Gly Tyr Gly Phe Asn
            180                 185                 190

Ile Thr Glu Ser Gly Ser Ala Asn Leu Asp Asp Lys Thr Met His Glu
        195                 200                 205

Leu Tyr Leu Trp Pro Phe Ala Asp Ala Ile Arg Ala Gly Ala Gly Ala
    210                 215                 220

Val Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Ala Ala His His Ala Gly Val Ser Gly Ala
            260                 265                 270

Leu Ala Gly Leu Asp Met Ser Met Pro Gly Asp Val Asp Tyr Asp Ser
        275                 280                 285

-continued

```
Gly Thr Ser Tyr Trp Gly Thr Asn Leu Thr Ile Ser Val Leu Asn Gly
    290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Trp Thr Pro Pro Asn Phe
                325                 330                 335

Ser Ser Trp Thr Arg Asp Glu Tyr Gly Phe Lys Tyr Tyr Tyr Val Ser
                340                 345                 350

Glu Gly Pro Tyr Glu Lys Val Asn Gln Phe Val Asn Val Gln Arg Asn
            355                 360                 365

His Ser Glu Leu Ile Arg Arg Ile Gly Ala Asp Ser Thr Val Leu Leu
    370                 375                 380

Lys Asn Asp Gly Ala Leu Pro Leu Thr Gly Lys Glu Arg Leu Val Ala
385                 390                 395                 400

Leu Ile Gly Glu Asp Ala Gly Ser Asn Pro Tyr Gly Ala Asn Gly Cys
                405                 410                 415

Ser Asp Arg Gly Cys Asp Asn Gly Thr Leu Ala Met Gly Trp Gly Ser
            420                 425                 430

Gly Thr Ala Asn Phe Pro Tyr Leu Val Thr Pro Glu Gln Ala Ile Ser
    435                 440                 445

Asn Glu Val Leu Lys Asn Lys Asn Gly Val Phe Thr Ala Thr Asp Asn
450                 455                 460

Trp Ala Ile Asp Gln Ile Glu Ala Leu Ala Lys Thr Ala Ser Val Ser
465                 470                 475                 480

Leu Val Phe Val Asn Ala Asp Ser Gly Glu Gly Tyr Ile Asn Val Asp
                485                 490                 495

Gly Asn Leu Gly Asp Arg Arg Asn Leu Thr Leu Trp Arg Asn Gly Asp
            500                 505                 510

Asn Val Ile Lys Ala Ala Ala Ser Asn Cys Asn Asn Thr Ile Val Ile
    515                 520                 525

Ile His Ser Val Gly Pro Val Leu Val Asn Glu Trp Tyr Asp Asn Pro
    530                 535                 540

Asn Val Thr Ala Ile Leu Trp Gly Gly Leu Pro Gly Gln Glu Ser Gly
545                 550                 555                 560

Asn Ser Leu Ala Asp Val Leu Tyr Gly Arg Val Asn Pro Gly Ala Lys
                565                 570                 575

Ser Pro Phe Thr Trp Gly Lys Thr Arg Glu Ala Tyr Gln Asp Tyr Leu
                580                 585                 590

Tyr Thr Glu Pro Asn Asn Gly Asn Gly Ala Pro Gln Glu Asp Phe Val
            595                 600                 605

Glu Gly Val Phe Ile Asp Tyr Arg Gly Phe Asp Lys Arg Asn Glu Thr
    610                 615                 620

Pro Ile Tyr Glu Phe Gly Tyr Gly Leu Ser Tyr Thr Thr Phe Asn Tyr
625                 630                 635                 640

Ser Asn Leu Gln Val Glu Val Leu Ser Ala Pro Ala Tyr Glu Pro Ala
                645                 650                 655

Ser Gly Glu Thr Glu Ala Ala Pro Thr Phe Gly Glu Val Gly Asn Ala
            660                 665                 670

Ser Asp Tyr Leu Tyr Pro Asp Gly Leu Gln Arg Ile Thr Lys Phe Ile
    675                 680                 685

Tyr Pro Trp Leu Asn Ser Thr Asp Leu Glu Ala Ser Ser Gly Asp Ala
690                 695                 700

Ser Tyr Gly Gln Asp Ala Ser Asp Tyr Leu Pro Glu Gly Ala Thr Asp
```

```
                    705                 710                 715                 720
               Gly Ser Ala Gln Pro Ile Leu Pro Ala Gly Gly Ala Gly Gly Asn
                           725                 730                 735

Pro Arg Leu Tyr Asp Glu Leu Ile Arg Val Ser Val Thr Ile Lys Asn
                           740                 745                 750

Thr Gly Lys Val Ala Gly Asp Glu Val Pro Gln Leu Tyr Val Ser Leu
                           755                 760                 765

Gly Gly Pro Asn Glu Pro Lys Ile Val Leu Arg Gln Phe Glu Arg Ile
                   770                 775                 780

Thr Leu Gln Pro Ser Lys Glu Thr Gln Trp Ser Thr Thr Leu Thr Arg
               785                 790                 795                 800

Arg Asp Leu Ala Asn Trp Asn Val Glu Thr Gln Asp Trp Glu Ile Thr
                               805                 810                 815

Ser Tyr Pro Lys Met Val Phe Ala Gly Ser Ser Arg Lys Leu Pro
                           820                 825                 830

Leu Arg Ala Ser Leu Pro Thr Val His
                       835                 840

<210> SEQ ID NO 3
<211> LENGTH: 32
<212> TYPE: DNA
<213> ORGANISM: Artificial Sequence
<220> FEATURE:
<223> OTHER INFORMATION: Synthetically generated primer

<400> SEQUENCE: 3
tatgccggga gacgtcgatt tcgacagtgg ca                                      32

<210> SEQ ID NO 4
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 4
tatggtctga gctacaccac ctttgaatac tcgaacctt                               39

<210> SEQ ID NO 5
<211> LENGTH: 2526
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5
gatgaattgg cctactcccc tccatactac ccatctccat gggctaacgg tcaaggtgat        60
tgggctgaag cttaccaaag agctgttgat attgtttctc aaatgacttt ggctgaaaag       120
gttaacttga ctactggtac tggttgggaa ttggaattgt gtgttggtca aactggtggt       180
gttccaagat tgggtattcc aggtatgtgt gctcaagatt ctccattggg tgttagagat       240
tctgactaca actctgcgtt ccctgccggt gtcaacgtgg ccgcaacctg gacaagaat        300 ctggcttacc ttcgtggcca ggctatgggt caggagttta gtgacaaggg tgctgatatc       360
caattgggtc cagctgccgg ccctctcggt agaagtcccg acgcggtcg taactgggag        420 ggcttctccc ccgaccccgc cctcagtggt gtgctctttg cagagacaat caagggtatt       480
caggatgctg gtgtggttgc aacggctaag cactacatcg cctacgagca ggagcatttc       540
```

| | | |
|---|---|---|
| cgtcaggcgc ctgaagctca aggctacgga ttcaatatta ccgagagtgg aagcgcgaac | 600 |
| ctcgacgata agactatgca tgagctgtac ctctggccct tcgcggatgc catccgtgca | 660 |
| ggtgccggtg ctgtgatgtg ctcgtacaac cagatcaaca acagctatgg ctgccaaaac | 720 |
| agctacactc tgaacaagct gctcaaggct gagctgggtt tccagggctt tgtcatgagt | 780 |
| gattgggcgg ctcaccatgc cggtgtgagt ggtgctttgg cgggattgga catgtctatg | 840 |
| ccgggagacg tcgatttcga cagtggcacg tcttactggg gtaccaactt gaccatcagt | 900 |
| gtgctcaacg ggacggtgcc ccaatggcgt gttgatgaca tggctgtccg catcatggcc | 960 |
| gcctactaca aggtcggccg tgaccgtctg tggactcctc ccaacttcag ctcatggacc | 1020 |
| agagatgaat acggcttcaa gtactactat gtctcggagg gaccgtatga aaggtcaac | 1080 |
| cagttcgtga acgtgcaacg caaccatagc gagttgatcc gccgtattgg agcagacagc | 1140 |
| acggtgctcc tcaagaacga tggcgctctt cccttgactg gaaaggagcg cttggtcgcc | 1200 |
| cttatcggag aagatgcggg ttccaatcct tatggtgcca acggctgcag tgaccgtggg | 1260 |
| tgcgacaatg gaacattggc gatgggctgg ggaagtggca ctgccaactt tccctacttg | 1320 |
| gtgaccccg agcaggccat ctcgaacgag gtgctcaaga acaagaatgg cgtattcact | 1380 |
| gcgaccgata actgggctat tgatcagatt gaggcgcttg ctaagaccgc cagtgtctct | 1440 |
| cttgtctttg tcaacgccga ctcggtgag ggttatatca atgtcgacgg aaacctgggt | 1500 |
| gaccgcagga acctgaccct gtggaggaac ggcgacaatg tgatcaaggc tgctgctagc | 1560 |
| aactgcaaca cacgatcgt tattattcac tctgtcggcc cagtcttggt taacgagtgg | 1620 |
| tacgacaacc ccaatgttac cgctattctc tggggtggtc ttcccggtca ggagtctggc | 1680 |
| aactccctcg ccgacgtgct ctacggccgt gtcaaccccg gtgccaagtc gcccttcacc | 1740 |
| tggggcaaga ctcgtgaggc ctaccaagat tacttgtaca ccgagcccaa caacggcaac | 1800 |
| ggagcgcccc aggaagactt cgtcgagggc gtcttcattg actaccgcgg atttgacaag | 1860 |
| cgcaacgaga ctcctatcta tgagttcggc tatggtctga gctacaccac cttcaactac | 1920 |
| tcgaaccttc aggtggaggt tctgagcgcc cctgcgtacg agcctgcttc gggcgagact | 1980 |
| gaggcagcgc cgactttcgg agaggtcgga aatgcgtcgg attacctcta ccccgatgga | 2040 |
| ctgcagagaa tcaccaagtt catctacccc tggctcaaca gtaccgatct tgaggcgtct | 2100 |
| tctgggatg ctagctatgg gcaggatgcc tcagactatc ttcccgaggg agccaccgat | 2160 |
| ggctctgcgc aaccgatcct gcctgccggt ggtggtgctg gcggcaaccc tcgcctgtac | 2220 |
| gacgagctca tccgcgtgtc ggtgactatc aagaacaccg gcaaggttgc gggtgatgaa | 2280 |
| gttcctcaac tgtatgtttc tcttggcggc cctaacgaac ccaagatcgt gctgcgtcaa | 2340 |
| ttcgagcgta tcacgctgca gccgtcgaaa gagacgcagt ggagcacaac tctgacgcgc | 2400 |
| cgtgaccttg cgaactggaa tgttgagacg caggactggg agattacgtc gtatcccaag | 2460 |
| atggtgtttg ccggaagctc ctcgcggaag ctgccgctcc gggcgtctct gcctactgtt | 2520 |
| cactaa | 2526 |

<210> SEQ ID NO 6
<211> LENGTH: 841
<212> TYPE: PRT
<213> ORGANISM: Artificial Sequence
<220> FEATURE:
<223> OTHER INFORMATION: Sequence synthetically translated from SEQ ID
      NO: 5

<400> SEQUENCE: 6

```
Asp Glu Leu Ala Tyr Ser Pro Pro Tyr Tyr Pro Ser Pro Trp Ala Asn
1               5                   10                  15
Gly Gln Gly Asp Trp Ala Glu Ala Tyr Gln Arg Ala Val Asp Ile Val
            20                  25                  30
Ser Gln Met Thr Leu Ala Glu Lys Val Asn Leu Thr Thr Gly Thr Gly
            35                  40                  45
Trp Glu Leu Glu Leu Cys Val Gly Gln Thr Gly Gly Val Pro Arg Leu
50                  55                  60
Gly Ile Pro Gly Met Cys Ala Gln Asp Ser Pro Leu Gly Val Arg Asp
65                  70                  75                  80
Ser Asp Tyr Asn Ser Ala Phe Pro Ala Gly Val Asn Val Ala Ala Thr
                85                  90                  95
Trp Asp Lys Asn Leu Ala Tyr Leu Arg Gly Gln Ala Met Gly Gln Glu
            100                 105                 110
Phe Ser Asp Lys Gly Ala Asp Ile Gln Leu Gly Pro Ala Ala Gly Pro
            115                 120                 125
Leu Gly Arg Ser Pro Asp Gly Gly Arg Asn Trp Glu Gly Phe Ser Pro
    130                 135                 140
Asp Pro Ala Leu Ser Gly Val Leu Phe Ala Glu Thr Ile Lys Gly Ile
145                 150                 155                 160
Gln Asp Ala Gly Val Val Ala Thr Ala Lys His Tyr Ile Ala Tyr Glu
                165                 170                 175
Gln Glu His Phe Arg Gln Ala Pro Glu Ala Gln Gly Tyr Gly Phe Asn
            180                 185                 190
Ile Thr Glu Ser Gly Ser Ala Asn Leu Asp Asp Lys Thr Met His Glu
            195                 200                 205
Leu Tyr Leu Trp Pro Phe Ala Asp Ala Ile Arg Ala Gly Ala Gly Ala
    210                 215                 220
Val Met Cys Ser Tyr Asn Gln Ile Asn Asn Ser Tyr Gly Cys Gln Asn
225                 230                 235                 240
Ser Tyr Thr Leu Asn Lys Leu Leu Lys Ala Glu Leu Gly Phe Gln Gly
                245                 250                 255
Phe Val Met Ser Asp Trp Ala Ala His His Ala Gly Val Ser Gly Ala
            260                 265                 270
Leu Ala Gly Leu Asp Met Ser Met Pro Gly Asp Val Asp Phe Asp Ser
    275                 280                 285
Gly Thr Ser Tyr Trp Gly Thr Asn Leu Thr Ile Ser Val Leu Asn Gly
    290                 295                 300
Thr Val Pro Gln Trp Arg Val Asp Asp Met Ala Val Arg Ile Met Ala
305                 310                 315                 320
Ala Tyr Tyr Lys Val Gly Arg Asp Arg Leu Trp Thr Pro Pro Asn Phe
                325                 330                 335
Ser Ser Trp Thr Arg Asp Glu Tyr Gly Phe Lys Tyr Tyr Val Ser
            340                 345                 350
Glu Gly Pro Tyr Glu Lys Val Asn Gln Phe Val Asn Val Gln Arg Asn
    355                 360                 365
His Ser Glu Leu Ile Arg Arg Ile Gly Ala Asp Ser Thr Val Leu Leu
    370                 375                 380
Lys Asn Asp Gly Ala Leu Pro Leu Thr Gly Lys Glu Arg Leu Val Ala
385                 390                 395                 400
Leu Ile Gly Glu Asp Ala Gly Ser Asn Pro Tyr Gly Ala Asn Gly Cys
                405                 410                 415
Ser Asp Arg Gly Cys Asp Asn Gly Thr Leu Ala Met Gly Trp Gly Ser
```

```
              420             425             430
Gly Thr Ala Asn Phe Pro Tyr Leu Val Thr Pro Glu Gln Ala Ile Ser
            435             440             445

Asn Glu Val Leu Lys Asn Lys Asn Gly Val Phe Thr Ala Thr Asp Asn
450             455             460

Trp Ala Ile Asp Gln Ile Glu Ala Leu Ala Lys Thr Ala Ser Val Ser
465             470             475             480

Leu Val Phe Val Asn Ala Asp Ser Gly Glu Gly Tyr Ile Asn Val Asp
                485             490             495

Gly Asn Leu Gly Asp Arg Arg Asn Leu Thr Leu Trp Arg Asn Gly Asp
            500             505             510

Asn Val Ile Lys Ala Ala Ser Asn Cys Asn Asn Thr Ile Val Ile
            515             520             525

Ile His Ser Val Gly Pro Val Leu Val Asn Glu Trp Tyr Asp Asn Pro
            530             535             540

Asn Val Thr Ala Ile Leu Trp Gly Gly Leu Pro Gly Gln Glu Ser Gly
545             550             555             560

Asn Ser Leu Ala Asp Val Leu Tyr Gly Arg Val Asn Pro Gly Ala Lys
                565             570             575

Ser Pro Phe Thr Trp Gly Lys Thr Arg Glu Ala Tyr Gln Asp Tyr Leu
            580             585             590

Tyr Thr Glu Pro Asn Asn Gly Asn Gly Ala Pro Gln Glu Asp Phe Val
            595             600             605

Glu Gly Val Phe Ile Asp Tyr Arg Gly Phe Asp Lys Arg Asn Glu Thr
            610             615             620

Pro Ile Tyr Glu Phe Gly Tyr Gly Leu Ser Tyr Thr Thr Phe Asn Tyr
625             630             635             640

Ser Asn Leu Gln Val Glu Val Leu Ser Ala Pro Ala Tyr Glu Pro Ala
                645             650             655

Ser Gly Glu Thr Glu Ala Ala Pro Thr Phe Gly Glu Val Gly Asn Ala
            660             665             670

Ser Asp Tyr Leu Tyr Pro Asp Gly Leu Gln Arg Ile Thr Lys Phe Ile
            675             680             685

Tyr Pro Trp Leu Asn Ser Thr Asp Leu Glu Ala Ser Ser Gly Asp Ala
690             695             700

Ser Tyr Gly Gln Asp Ala Ser Tyr Leu Pro Glu Gly Ala Thr Asp
705             710             715             720

Gly Ser Ala Gln Pro Ile Leu Pro Ala Gly Gly Ala Gly Asn
            725             730             735

Pro Arg Leu Tyr Asp Glu Leu Ile Arg Val Ser Val Thr Ile Lys Asn
            740             745             750

Thr Gly Lys Val Ala Gly Asp Glu Val Pro Gln Leu Tyr Val Ser Leu
            755             760             765

Gly Gly Pro Asn Glu Pro Lys Ile Val Leu Arg Gln Phe Glu Arg Ile
            770             775             780

Thr Leu Gln Pro Ser Lys Glu Thr Gln Trp Ser Thr Thr Leu Thr Arg
785             790             795             800

Arg Asp Leu Ala Asn Trp Asn Val Glu Thr Gln Asp Trp Glu Ile Thr
                805             810             815

Ser Tyr Pro Lys Met Val Phe Ala Gly Ser Ser Ser Arg Lys Leu Pro
            820             825             830

Leu Arg Ala Ser Leu Pro Thr Val His
            835             840
```

<210> SEQ ID NO 7
<211> LENGTH: 2526
<212> TYPE: DNA
<213> ORGANISM: Artificial Sequence
<220> FEATURE:
<223> OTHER INFORMATION: Synthetically generated DNA encoding a modified enzyme

<400> SEQUENCE: 7

| | |
|---|---:|
| gatgaattgg cctactcccc tccatactac ccatctccat gggctaacgg tcaaggtgat | 60 |
| tgggctgaag cttaccaaag agctgttgat attgtttctc aaatgacttt ggctgaaaag | 120 |
| gttaacttga ctactggtac tggttgggaa ttggaattgt gtgttggtca aactggtggt | 180 |
| gttccaagat tgggtattcc aggtatgtgt gctcaagatt ctccattggg tgttagagat | 240 |
| tctgactaca actctgcgtt ccctgccggt gtcaacgtgg ccgcaacctg gacaagaat | 300 |
| ctggcttacc ttcgtggcca ggctatgggt caggagttta gtgacaaggg tgctgatatc | 360 |
| caattgggtc cagctgccgg ccctctcggt agaagtcccg acggcggtcg taactgggag | 420 |
| ggcttctccc ccgacccggc cctcagtggt gtgctctttg cagagacaat caagggtatt | 480 |
| caggatgctg gtgtggttgc aacggctaag cactacatcg cctacgagca ggagcatttc | 540 |
| cgtcaggcgc tgaagctcaa ggctacggat tcaatatta ccgagagtgg aagcgcgaac | 600 |
| ctcgacgata agactatgca tgagctgtac ctctggccct cgcggatgc catccgtgca | 660 |
| ggtgccggtg ctgtgatgtg ctcgtacaac cagatcaaca acagctatgg ctgccaaaac | 720 |
| agctacactc tgaacaagct gctcaaggct gagctgggtt ccagggctt tgtcatgagt | 780 |
| gattgggcgg ctcaccatgc cggtgtgagt ggtgcttt gg cgggattgga catgtctatg | 840 |
| ccgggagacg tcgattacga cagtggcacg tcttactggg gtaccaactt gaccatcagt | 900 |
| gtgctcaacg gacggtgccc caatggcgt gttgatgaca tggctgtccg catcatggcc | 960 |
| gcctactaca aggtcggccg tgaccgtctg tggactcctc ccaacttcag ctcatggacc | 1020 |
| agagatgaat acggcttcaa gtactactat gtctcggagg gaccgtatga aaggtcaac | 1080 |
| cagttcgtga acgtgcaacg caaccatagc gagttgatcc gccgtattgg agcagacagc | 1140 |
| acggtgctcc tcaagaacga tggcgctctt cccttgactg gaaaggagcg cttggtcgcc | 1200 |
| cttatcggag aagatgcggg ttccaatcct tatggtgcca acggctgcag tgaccgtggg | 1260 |
| tgcgacaatg aacattggc gatgggctgg ggaagtggca ctgccaactt ccctacttg | 1320 |
| gtgaccccg agcaggccat ctcgaacgag gtgctcaaga caagaatgg cgtattcact | 1380 |
| gcgaccgata actgggctat tgatcagatt gaggcgcttg ctaagaccgc cagtgtctct | 1440 |
| cttgtctttg tcaacgccga ctctggtgag ggttatatca atgtcgacgg aaacctgggt | 1500 |
| gaccgcagga acctgaccct gtggaggaac ggcgacaatg tgatcaaggc tgctgctagc | 1560 |
| aactgcaaca cacgatcgt tattattcac tctgtcggcc cagtcttggt taacgagtgg | 1620 |
| tacgacaacc ccaatgttac cgctattctc tggggtggtc ttcccggtca ggagtctggc | 1680 |
| aactccctcg ccgacgtgct ctacggccgt gtcaaccccg gtgccaagtc gcccttcacc | 1740 |
| tggggcaaga ctcgtgaggc ctaccaagat tacttgtaca ccgagcccaa caacggcaac | 1800 |
| ggagcgcccc aggaagactt cgtcgagggc gtcttcattg actaccgcgg atttgacaag | 1860 |
| cgcaacgaga ctcctatcta tgagttcggc tatggtctga gctacaccac ctttgaatac | 1920 |
| tcgaaccttc agtggaggt tctgagcgcc cctgcgtacg agcctgcttc gggcgagact | 1980 |
| gaggcagcgc cgactttcgg agaggtcgga aatgcgtcgg attacctcta ccccgatgga | 2040 |

```
ctgcagagaa tcaccaagtt catctacccc tggctcaaca gtaccgatct tgaggcgtct      2100
tctggggatg ctagctatgg caggatgcc tcagactatc ttcccgaggg agccaccgat       2160
ggctctgcgc aaccgatcct gcctgccggt ggtggtgctg gcggcaaccc tcgcctgtac     2220
gacgagctca tccgcgtgtc ggtgactatc aagaacaccg gcaaggttgc gggtgatgaa     2280
gttcctcaac tgtatgtttc tcttggcggc cctaacgaac ccaagatcgt gctgcgtcaa     2340
ttcgagcgta tcacgctgca gccgtcgaaa gagacgcagt ggagcacaac tctgacgcgc     2400
cgtgaccttg cgaactggaa tgttgagacg caggactggg agattacgtc gtatcccaag     2460
atggtgtttg ccggaagctc ctcgcggaag ctgccgctcc gggcgtctct gcctactgtt     2520
cactaa                                                                 2526
```

<210> SEQ ID NO 8
<211> LENGTH: 841
<212> TYPE: PRT
<213> ORGANISM: Artificial Sequence
<220> FEATURE:
<223> OTHER INFORMATION: Sequence synthetically translated from SEQ ID NO: 7

<400> SEQUENCE: 8

```
Asp Glu Leu Ala Tyr Ser Pro Pro Tyr Tyr Pro Ser Pro Trp Ala Asn
1               5                   10                  15

Gly Gln Gly Asp Trp Ala Glu Ala Tyr Gln Arg Ala Val Asp Ile Val
            20                  25                  30

Ser Gln Met Thr Leu Ala Glu Lys Val Asn Leu Thr Thr Gly Thr Gly
        35                  40                  45

Trp Glu Leu Glu Leu Cys Val Gly Gln Thr Gly Gly Val Pro Arg Leu
    50                  55                  60

Gly Ile Pro Gly Met Cys Ala Gln Asp Ser Pro Leu Gly Val Arg Asp
65                  70                  75                  80

Ser Asp Tyr Asn Ser Ala Phe Pro Ala Gly Val Asn Val Ala Ala Thr
                85                  90                  95

Trp Asp Lys Asn Leu Ala Tyr Leu Arg Gly Gln Ala Met Gly Gln Glu
            100                 105                 110

Phe Ser Asp Lys Gly Ala Asp Ile Gln Leu Gly Pro Ala Ala Gly Pro
        115                 120                 125

Leu Gly Arg Ser Pro Asp Gly Gly Arg Asn Trp Glu Gly Phe Ser Pro
    130                 135                 140

Asp Pro Ala Leu Ser Gly Val Leu Phe Ala Glu Thr Ile Lys Gly Ile
145                 150                 155                 160

Gln Asp Ala Gly Val Val Ala Thr Ala Lys His Tyr Ile Ala Tyr Glu
                165                 170                 175

Gln Glu His Phe Arg Gln Ala Pro Glu Ala Gln Gly Tyr Gly Phe Asn
            180                 185                 190

Ile Thr Glu Ser Gly Ser Ala Asn Leu Asp Asp Lys Thr Met His Glu
        195                 200                 205

Leu Tyr Leu Trp Pro Phe Ala Asp Ala Ile Arg Ala Gly Ala Gly Ala
    210                 215                 220

Val Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Ala Ala His His Ala Gly Val Ser Gly Ala
```

```
                260             265             270
Leu Ala Gly Leu Asp Met Ser Met Pro Gly Asp Val Asp Tyr Asp Ser
            275             280             285
Gly Thr Ser Tyr Trp Gly Thr Asn Leu Thr Ile Ser Val Leu Asn Gly
            290             295             300
Thr Val Pro Gln Trp Arg Val Asp Asp Met Ala Val Arg Ile Met Ala
305             310             315             320
Ala Tyr Tyr Lys Val Gly Arg Asp Arg Leu Trp Thr Pro Pro Asn Phe
            325             330             335
Ser Ser Trp Thr Arg Asp Glu Tyr Gly Phe Lys Tyr Tyr Val Ser
            340             345             350
Glu Gly Pro Tyr Glu Lys Val Asn Gln Phe Val Asn Val Gln Arg Asn
            355             360             365
His Ser Glu Leu Ile Arg Arg Ile Gly Ala Asp Ser Thr Val Leu Leu
            370             375             380
Lys Asn Asp Gly Ala Leu Pro Leu Thr Gly Lys Glu Arg Leu Val Ala
385             390             395             400
Leu Ile Gly Glu Asp Ala Gly Ser Asn Pro Tyr Gly Ala Asn Gly Cys
            405             410             415
Ser Asp Arg Gly Cys Asp Asn Gly Thr Leu Ala Met Gly Trp Gly Ser
            420             425             430
Gly Thr Ala Asn Phe Pro Tyr Leu Val Thr Pro Glu Gln Ala Ile Ser
            435             440             445
Asn Glu Val Leu Lys Asn Lys Asn Gly Val Phe Thr Ala Thr Asp Asn
            450             455             460
Trp Ala Ile Asp Gln Ile Glu Ala Leu Ala Lys Thr Ala Ser Val Ser
465             470             475             480
Leu Val Phe Val Asn Ala Asp Ser Gly Glu Gly Tyr Ile Asn Val Asp
            485             490             495
Gly Asn Leu Gly Asp Arg Arg Asn Leu Thr Leu Trp Arg Asn Gly Asp
            500             505             510
Asn Val Ile Lys Ala Ala Ala Ser Asn Cys Asn Asn Thr Ile Val Ile
            515             520             525
Ile His Ser Val Gly Pro Val Leu Val Asn Glu Trp Tyr Asp Asn Pro
            530             535             540
Asn Val Thr Ala Ile Leu Trp Gly Gly Leu Pro Gly Gln Glu Ser Gly
545             550             555             560
Asn Ser Leu Ala Asp Val Leu Tyr Gly Arg Val Asn Pro Gly Ala Lys
            565             570             575
Ser Pro Phe Thr Trp Gly Lys Thr Arg Glu Ala Tyr Gln Asp Tyr Leu
            580             585             590
Tyr Thr Glu Pro Asn Asn Gly Asn Gly Ala Pro Gln Glu Asp Phe Val
            595             600             605
Glu Gly Val Phe Ile Asp Tyr Arg Gly Phe Asp Lys Arg Asn Glu Thr
            610             615             620
Pro Ile Tyr Glu Phe Gly Tyr Gly Leu Ser Tyr Thr Thr Phe Glu Tyr
625             630             635             640
Ser Asn Leu Gln Val Glu Val Leu Ser Ala Pro Ala Tyr Glu Pro Ala
            645             650             655
Ser Gly Glu Thr Glu Ala Ala Pro Thr Phe Gly Glu Val Gly Asn Ala
            660             665             670
Ser Asp Tyr Leu Tyr Pro Asp Gly Leu Gln Arg Ile Thr Lys Phe Ile
            675             680             685
```

```
Tyr Pro Trp Leu Asn Ser Thr Asp Leu Glu Ala Ser Ser Gly Asp Ala
        690             695             700

Ser Tyr Gly Gln Asp Ala Ser Asp Tyr Leu Pro Glu Gly Ala Thr Asp
705             710             715                         720

Gly Ser Ala Gln Pro Ile Leu Pro Ala Gly Gly Ala Gly Gly Asn
            725             730             735

Pro Arg Leu Tyr Asp Glu Leu Ile Arg Val Ser Val Thr Ile Lys Asn
            740             745             750

Thr Gly Lys Val Ala Gly Asp Glu Val Pro Gln Leu Tyr Val Ser Leu
        755             760             765

Gly Gly Pro Asn Glu Pro Lys Ile Val Leu Arg Gln Phe Glu Arg Ile
    770             775             780

Thr Leu Gln Pro Ser Lys Glu Thr Gln Trp Ser Thr Thr Leu Thr Arg
785             790             795                         800

Arg Asp Leu Ala Asn Trp Asn Val Glu Thr Gln Asp Trp Glu Ile Thr
            805             810             815

Ser Tyr Pro Lys Met Val Phe Ala Gly Ser Ser Ser Arg Lys Leu Pro
            820             825             830

Leu Arg Ala Ser Leu Pro Thr Val His
        835             840
```

BETA-GLUCOSIDASE HAVING IMPROVED ENZYMATIC ACTIVITY

FIELD OF THE INVENTION

The present invention relates to a beta-glucosidase, and more particularly to a beta-glucosidase having improved enzymatic activity.

BACKGROUND OF THE INVENTION

Cellulose is one of the major components in plant cell wall and is also a major resource of biomass on earth. Hence, many enzymes that degrade cellulose can be widely applied in many different industries. Cellulose is a polysaccharide composed of glucose units linked by β-1,4-glycosidic bond. These polysaccharides organize tightly together to form crystalline cellulose in order to defense external destruction. On the other hand, many kinds of herbivores and microbes need to degrade cellulose from plant to glucose as an energy source by different degrading enzymes including cellulase, xylanase and so on. The catalytic mechanism of cellulase involves hydrolyzing the β-1,4-glycosidic bond between two sugar units by acid-base interaction. Cellulase can be generally divided into three groups including endoglucanase (E.C. 3.2.1.4), cellobiohydrolase (E.C. 3.2.1.91) and beta-glucosidase (E.C. 3.2.1.21). Endoglucanase can randomly degrade cellulose into many small fragments. Cellobiohydrolase can degrade cellulose from reducing end or non-reducing end to release main product, cellobiose. Beta-glucosidase can degrade cellobiose into simple sugar glucose.

Beta-glucosidase widely exists in plants, insects, yeasts, *Aspergillus, Trichoderma* and bacteria in nature. It participates in the sugar metabolism of organisms and plays an important role in maintaining the normal physiological functions of organisms. Currently, many researches try to obtain better enzymes by either screening in nature or modifying existing enzymes. The present invention intends to analyze the enzyme structure of beta-glucosidase for finding out the key amino acid important to the enzymatic activity, and further modify the enzyme, so as to improve its enzymatic activity and thus increase its industrial value.

SUMMARY OF THE INVENTION

An object of the present invention is to modify an existing beta-glucosidase by means of structural analysis and site-directed mutagenesis for improving the enzymatic activity of the beta-glucosidase and further increasing its application potential and economic value in industry.

According to an aspect of the present invention, there is provided a beta-glucosidase comprising a modified amino acid sequence of SEQ ID NO: 2, wherein the modification is a substitution of tyrosine at position 286 with phenylalanine. The gene encoding the amino acid sequence of SEQ ID NO: 2 is AnBgl gene isolated from *Aspergillus niger* SH2. The beta-glucosidase has a full length amino acid sequence of SEQ ID NO: 6.

According to another aspect of the present invention, there is provided a beta-glucosidase comprising a modified amino acid sequence of SEQ ID NO: 2, wherein the modification is a substitution of asparagine at position 639 with glutamate. The gene encoding the amino acid sequence of SEQ ID NO: 2 is AnBgl gene isolated from *Aspergillus niger* SH2. The beta-glucosidase has a full length amino acid sequence of SEQ ID NO: 8.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the wild type beta-glucosidase AnBgl;

FIG. 2 shows the mutagenic primer sequences for site-directed mutagenesis;

FIG. 3 shows the nucleotide sequence and the amino acid sequence of the Y286F mutant;

FIG. 4 shows the nucleotide sequence and the amino acid sequence of the N639E mutant;

DETAILED DESCRIPTION OF THE PREFERRED EMBODIMENT

Figure 5:
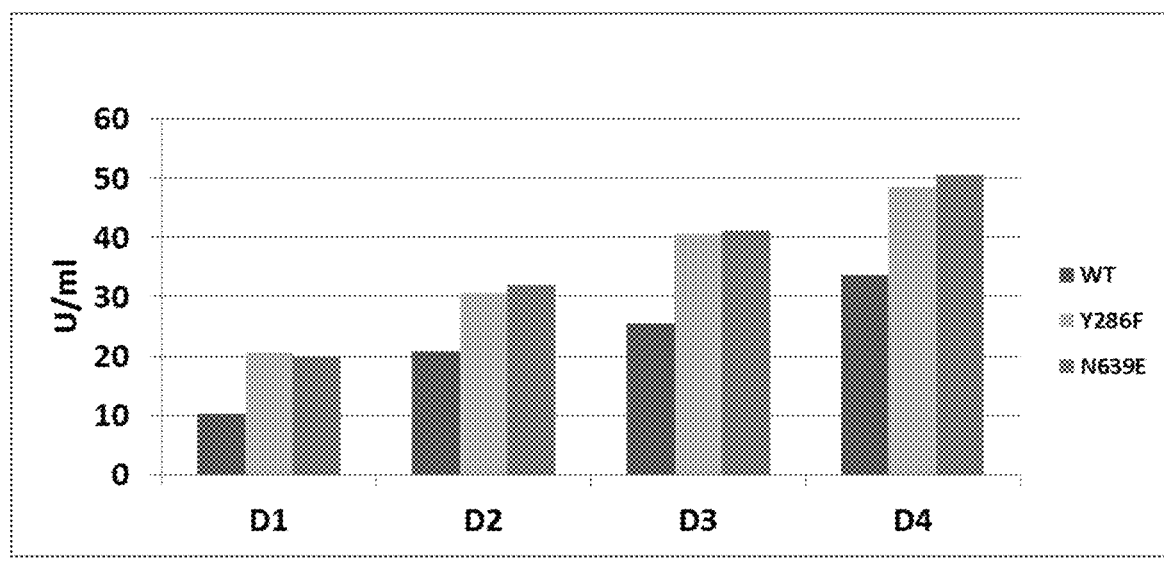
FIG. 5 shows the activity analysis of the wild type AnBgl, the Y286F mutant and the N639E mutant in flask.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The beta-glucosidase from *Aspergillus* spp. is one of the beta-glucosidases widely used in the feed industry. In the present invention, the primers of the beta-glucosidase from *Aspergillus* spp. were designed based on the gene sequence in the gene bank. A gene segment called AnBgl gene was obtained by gene fishing from the genome of the laboratory-preserved strain *Aspergillus niger* SH2. After alignment, it was observed that the AnBgl gene is 98% similar to the beta-glucosidase A gene of *Aspergillus niger* CBS 513.88, and the amino acid sequence of the AnBgl gene is 100% similar to the beta-glucosidase (Gene bank: AIE48478.1) of *Aspergillus niger*.

The amino acid sequence of the AnBgl gene fished from *Aspergillus niger* SH2 was used for protein structure modeling by SWISS-MODEL. After obtaining the modeled protein structure, the protein structure alignment by BLAST was performed, and it was found that the closest structure is beta-glucosidase 1 (PDB ID: 4IIB) from *Aspergillus aculeatus* with 83% similarity. Then the modeled protein structure of the beta-glucosidase AnBgl from *Aspergillus niger* SH2 was further analyzed by PyMOL for alignment with the beta-glucosidase (PDB ID: 4IIB) from *Aspergillus aculeatus* and the beta-glucosidase (AFU51372.1) from *Thermoascus aurantiacus*, both of which have higher specific activities.

According to the alignment result, it was found that in the protein structures of both the beta-glucosidase from *Aspergillus aculeatus* and the beta-glucosidase from *Thermoascus aurantiacus*, the amino acid residue at position 286 in the active site is phenylalanine. While in the protein structure of the beta-glucosidase AnBgl from *Aspergillus niger* SH2, the corresponding amino acid residue is tyrosine at position 286. Therefore, the present invention intends to substitute the tyrosine (Y) at position 286 of the beta-glucosidase AnBgl from *Aspergillus niger* SH2 with phenylalanine (F) to obtain the Y286F mutant protein in order to improve the enzymatic activity of the beta-glucosidase AnBgl.

In addition, the glycosylation sites of Asn-Xaa-Ser/Thr in the amino acid sequences of both the beta-glucosidase AnBgl from *Aspergillus niger* SH2 and the beta-glucosidase from *Thermoascus aurantiacus* were predicted by NetNGlyc 1.0 Server and then compared to find out a target site where there is a glycosylation sequence in the beta-glucosidase AnBgl from *Aspergillus niger* SH2 and there is no glycosylation sequence in the beta-glucosidase AnBgl from *Thermoascus aurantiacus*. It was found that there is a glycosylation sequence including the asparagine at position 639 in the beta-glucosidase AnBgl from *Aspergillus niger* SH2, while in the corresponding site of the beta-glucosidase from *Thermoascus aurantiacus*, there is no glycosylation sequence and the corresponding amino acid residue is glutamate. Therefore, the present invention intends to substitute the asparagine (N) at position 639 of the beta-glucosidase AnBgl from *Aspergillus niger* SH2 with glutamate (E) to obtain the N639E mutant protein in order to improve the enzymatic activity of the beta-glucosidase AnBgl.

The enzyme modification processes and the resulted beta-glucosidases are described in detail as follows.

Figure 1:
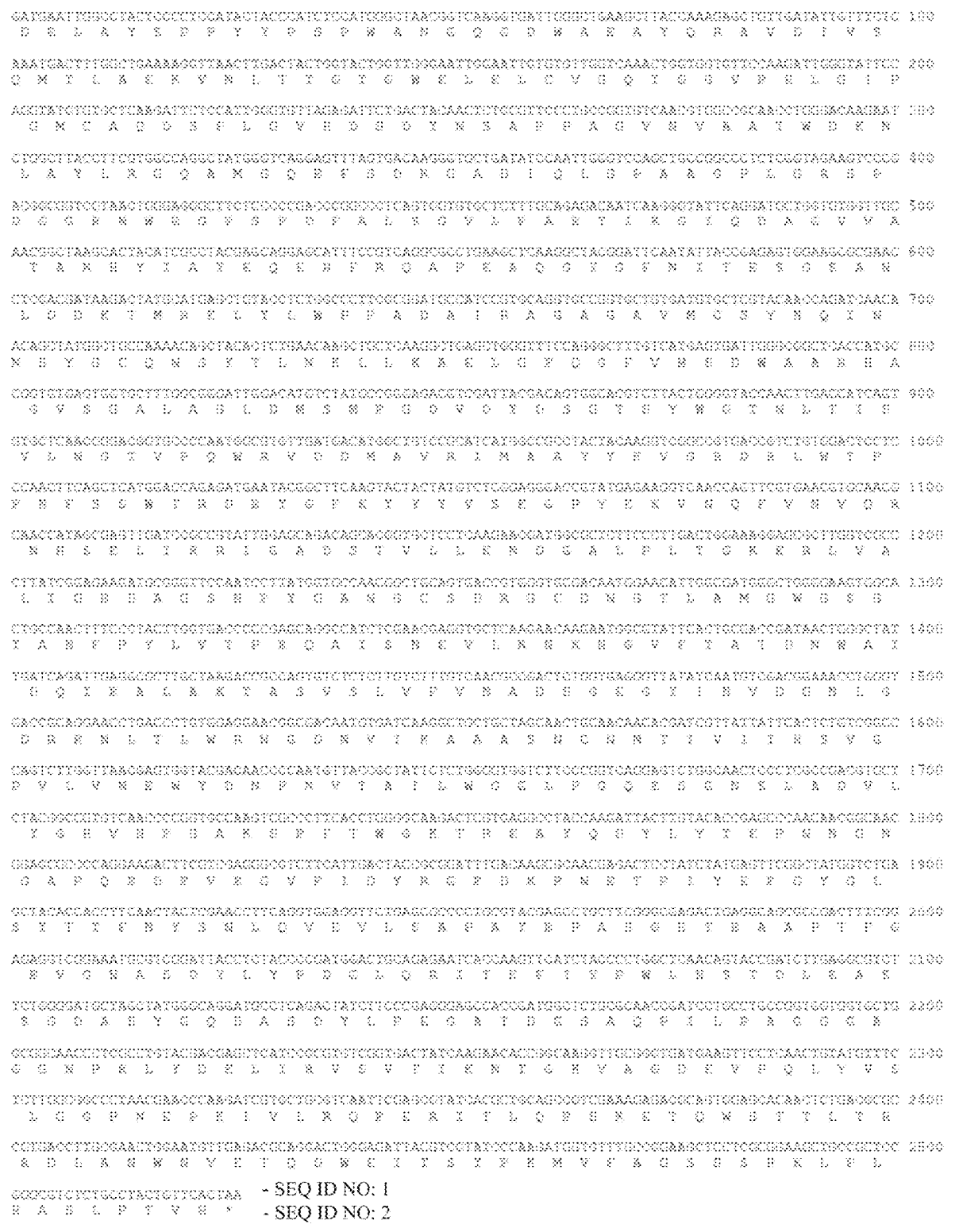

FIG. 1 shows the nucleotide sequence and the amino acid sequence of the wild type beta-glucosidase AnBgl from *Aspergillus niger* SH2, wherein the AnBgl gene includes 2526 base pairs (the nucleotide sequence was numbered as SEQ ID NO: 1) and encodes 841 amino acids (the amino acid sequence was numbered as SEQ ID NO: 2). The AnBgl gene was cloned into pPICZaA vector by EcoRI and NotI.

The two mutated genes of AnBgl were obtained by site-directed mutagenesis. Particularly, these mutated sequences were obtained by polymerase chain reaction method using the wild type AnBgl gene as the template and using the mutagenic primers shown in FIG. 2. Y286F means the tyrosine at position 286 was substituted with phenylalanine, and the mutagenic primer Y286F was numbered as SEQ ID NO: 3. N639E means the asparagine at position 639 was substituted with glutamate, and the mutagenic primer N639E was numbered as SEQ ID NO: 4. Therefore, the two mutated genes of AnBgl obtained by site-directed mutagenesis in the present invention were Y286F and N639E.

Figure 3:
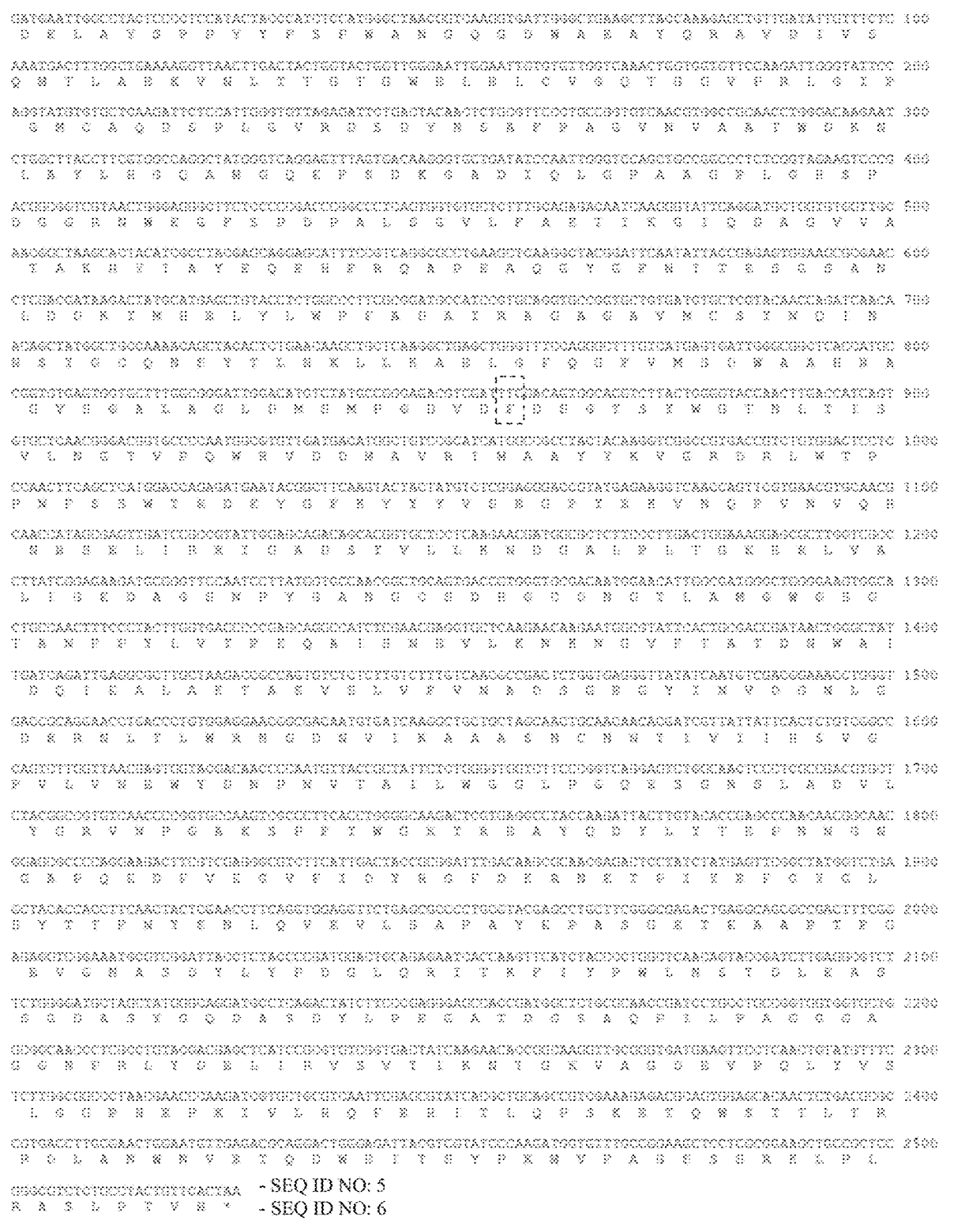
Figure 4:
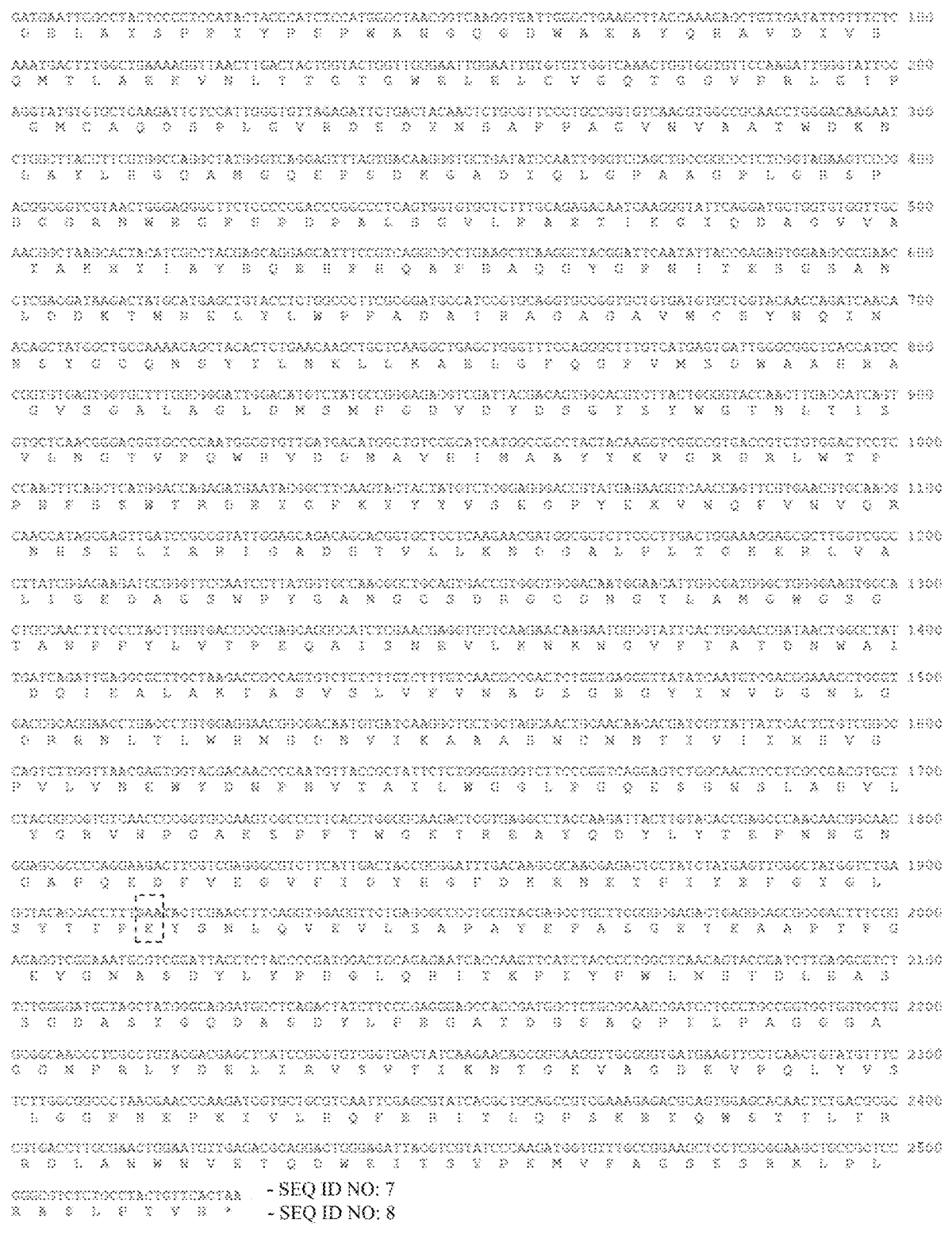

FIG. 3 and FIG. 4 show the nucleotide sequences and the amino acid sequences of the two mutants. FIG. 3 shows the nucleotide sequence and the amino acid sequence of the Y286F mutant, wherein the nucleotide sequence was numbered as SEQ ID NO: 5, the amino acid sequence was numbered as SEQ ID NO: 6, and the tyrosine at position 286 was substituted with phenylalanine. FIG. 4 shows the nucleotide sequence and the amino acid sequence of the N639E mutant, wherein the nucleotide sequence was numbered as SEQ ID NO: 7, the amino acid sequence was numbered as SEQ ID NO: 8, and the asparagine at position 639 was substituted with glutamate.

The modified DNA plasmids were linearized by PmeI and then transformed into *Pichia pastoris* X33 by electroporation. The transformants were selected on YPD plates containing 100 μg/ml zeocin and cultured at 30° C. for 2 days. The selected colonies were inoculated in 5 ml of YPD at 30° C. and then amplified in 50 ml of BMGY at 30° C. for 24 hours. The cells were harvested and then resuspended in 20 ml of BMMY to induce protein expression for 4 days. The samples were collected at different time points for every 24 hours, and meanwhile, the methanol was added into the flask to the final concentration of 1%. The cells were harvested by centrifugation at 3500 rpm and the supernatant was collected for protein purification and activity determination.

The beta-glucosidase activity analysis was determined by the measurement of released nitrophenol that is a chromogenic product from the hydrolysis of the substrate p-nitrophenyl-β-D-xylopyranoside (pNPG) by the beta-glucosidase and further calculated to determine the enzymatic activity of the beta-glucosidase. Basically, the reaction mixture composed of 0.2 ml of 5 mM p-nitrophenyl-β-D-xylopyranoside and the diluted enzyme protein sample in citric-phosphate buffer, pH 5.0, was incubated at 60° C. for 10 minutes. The reaction was then stopped by adding 0.75 ml of 2 M $Na_2CO_3$. Finally, the absorption of OD410 nm was detected to determine the activity of the beta-glucosidase.

FIG. 5 shows the activity analysis of the wild type AnBgl, the Y286F mutant and the N639E mutant in flask, wherein D1 to D4 represent the collected supernatants of the induced proteins at day 1 (D1) to day 4 (D4), respectively. It was observed from FIG. 5 that the activities of the beta-glucosidases for the Y286F mutant and the N639E mutant were both higher than that of the wild type (WT) AnBgl after methanol induction in D1 to D4.

Figure 6:
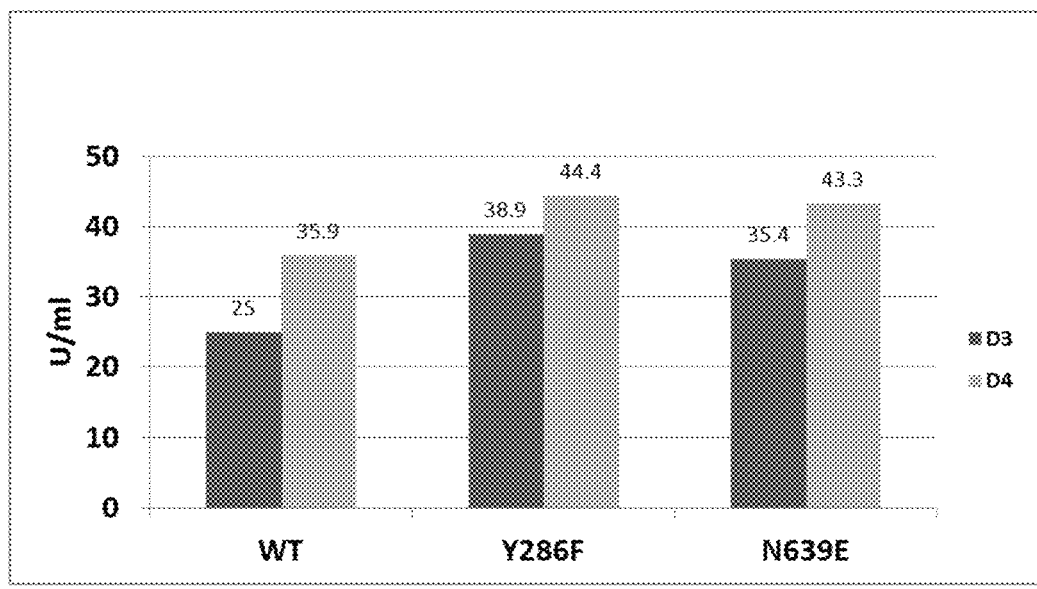
FIG. 6 shows the activity analysis of the wild type AnBgl, the Y286F mutant and the N639E mutant with the same protein concentration.

Then the protein concentrations of the wild type AnBgl, the Y286F mutant and the N639E mutant were adjusted to be consistent with each other for further activity analysis and comparison. FIG. 6 shows the activity analysis of the wild type AnBgl, the Y286F mutant and the N639E mutant with the same protein concentration. It was observed from FIG. 6 that the activities of the beta-glucosidases of the Y286F mutant and the N639E mutant were both higher than that of the wild type (WT) AnBgl as well when the enzymatic activities were determined with the same protein concentration.

Figure 7:
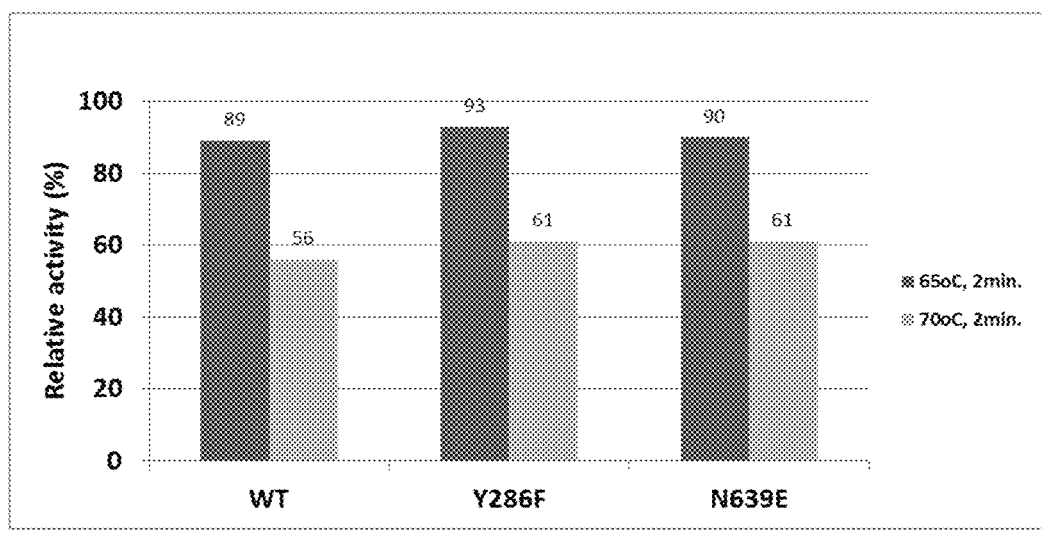
FIG. 7 shows the thermostability analysis of the wild type AnBgl, the Y286F mutant and the N639E mutant.

In addition, the thermostability analysis of the beta-glucosidase was also performed. The normalized protein samples of the wild type AnBgl, the Y286F mutant and the N639E mutant were individually treated at 65° C. and 70° C. for 2 minutes for subsequent activity analysis and comparison. FIG. 7 shows the thermostability analysis of the wild type AnBgl, the Y286F mutant and the N639E mutant. It was observed from FIG. 7 that the activities of the beta-glucosidases of the Y286F mutant and the N639E mutant after heat treatment at 65° C. and 70° C. for 2 minutes were both slightly higher than that of the wild type (WT) AnBgl.

In conclusion, to improve the enzymatic activity of the beta-glucosidase AnBgl, the present invention chose some potential amino acids according to its structural analysis and further modified this enzyme by rational design. As a result, the two mutants including Y286F and N639E both showed higher enzymatic activities when compared to the wild type protein, and also showed better thermostabilities when compared to the wild type protein. Therefore, the present invention successfully improves the enzymatic activity of the beta-glucosidase by Y286F and N639E modifications, so the production cost of the beta-glucosidase can be reduced to further increase its application potential and economic value in industry.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A beta-glucosidase comprising the amino acid sequence of SEQ ID NO: 2, with the exception of a substitution of tyrosine at position 286 of SEQ ID NO: 2 with phenylalanine.

2. The beta-glucosidase according to claim 1, wherein a gene encoding the amino acid sequence of SEQ ID NO: 2 is an AnBgl gene isolated from *Aspergillus niger* SH2.

3. The beta-glucosidase according to claim 1, wherein said beta-glucosidase comprises the full length amino acid sequence of SEQ ID NO: 6.

4. A beta-glucosidase comprising the amino acid sequence of SEQ ID NO: 2, with the exception of a substitution of asparagine at position 639 of SEQ ID NO: 2 with glutamate.

5. The beta-glucosidase according to claim 1, wherein a gene encoding the amino acid sequence of SEQ ID NO: 2 is an AnBgl gene isolated from *Aspergillus niger* SH2.

6. The beta-glucosidase according to claim 1, wherein said beta-glucosidase comprises the full length amino acid sequence of SEQ ID NO: 8.

* * * * *